(12) United States Patent
GrosJean et al.

(10) Patent No.: US 7,169,122 B2
(45) Date of Patent: Jan. 30, 2007

(54) PLACEBO-TYPE COMPRESSION ORTHOSIS

(75) Inventors: Eric GrosJean, Epinal (FR); Joel Mathieu, Eloyes (FR); Christian Gardon-Mollard, Chamalieres (FR)

(73) Assignee: Innothera Topic International, Arcueil (FR)

( * ) Notice: Subject to any disclaimer, the term of this patent is extended or adjusted under 35 U.S.C. 154(b) by 370 days.

(21) Appl. No.: 10/204,410

(22) PCT Filed: Feb. 27, 2001

(86) PCT No.: PCT/FR01/00567

§ 371 (c)(1),
(2), (4) Date: Dec. 12, 2002

(87) PCT Pub. No.: WO01/64152

PCT Pub. Date: Sep. 7, 2001

(65) Prior Publication Data
US 2003/0125655 A1    Jul. 3, 2003

(30) Foreign Application Priority Data
Feb. 29, 2000    (FR) .................................. 00 02527

(51) Int. Cl.
*A61F 13/00* (2006.01)
(52) U.S. Cl. ............................ 602/60; 602/61; 602/62; 602/63; 602/75
(58) Field of Classification Search ..................... 2/240, 2/409; 602/41, 53, 75–76, 60–63
See application file for complete search history.

(56) References Cited
U.S. PATENT DOCUMENTS

| 4,172,456 A | 10/1979 | Zens |
| 4,422,307 A | 12/1983 | Thorneburg |
| 4,520,635 A | 6/1985 | Shields et al. |
| 4,522,044 A | 6/1985 | Lineberry et al. |
| 4,527,402 A | 7/1985 | Swallow et al. |
| 4,745,917 A | 5/1988 | Hasty et al. |
| 5,945,215 A * | 8/1999 | Bersted et al. .............. 428/364 |
| 6,223,782 B1 * | 5/2001 | Watkins .................. 139/383 R |

FOREIGN PATENT DOCUMENTS

| FR | 688.378 | 1/1930 |
| FR | 1.122.832 | 9/1956 |
| FR | 2.017.339 | 5/1970 |

(Continued)

*Primary Examiner*—Michael A. Brown
(74) *Attorney, Agent, or Firm*—Jacobson Holman PLLC

(57) ABSTRACT

The surgical stocking made by knitting a knitting yarn together with an extensible weft yarn is a placebo type stocking suitable for exerting compressive pressure at the ankle of less than 8 mmHg, and preferably less than 5 mmHg. It is intended for double blind tests versus placebo using a product having the same structure, the same visual appearance, and the same feel as an active stocking but compression that is negligible and thigh/ankle degressivity that is close to unity. The weft yarn presents mass per unit length lying in the range 250 dtex to 600 dtex, preferably in the range 350 dtex to 500 dtex, with the proportion of elastic material being less than 25% and preferably less than 20% of the total weight of the thread. Its elongation capacity lies in the range 200% to 350%, preferably in the range 200% to 300%, but its springiness (II) is very different from that of an elastic stocking (I).

8 Claims, 2 Drawing Sheets

FOREIGN PATENT DOCUMENTS

| | | |
|---|---|---|
| FR | 2 432 867 | 10/1978 |
| FR | 2 588 890 A1 | 10/1985 |
| FR | 2588890 A * | 4/1987 |
| FR | 2 654 925 A1 | 11/1989 |
| FR | 2654925 A * | 5/1991 |
| FR | 2 758 299 A1 | 1/1997 |

* cited by examiner

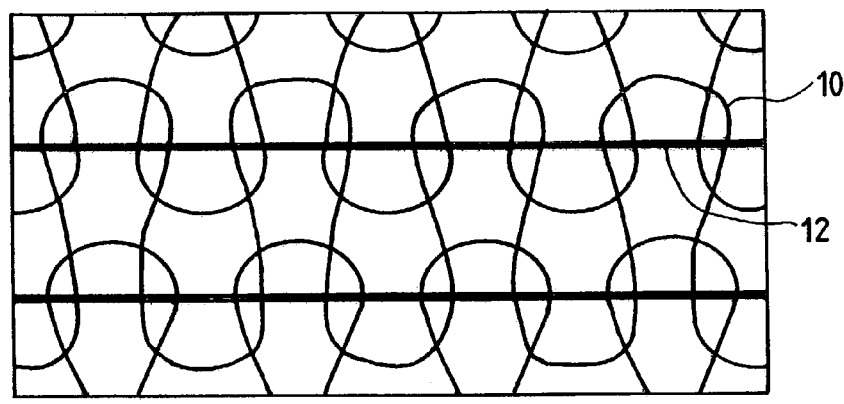
FIG_1
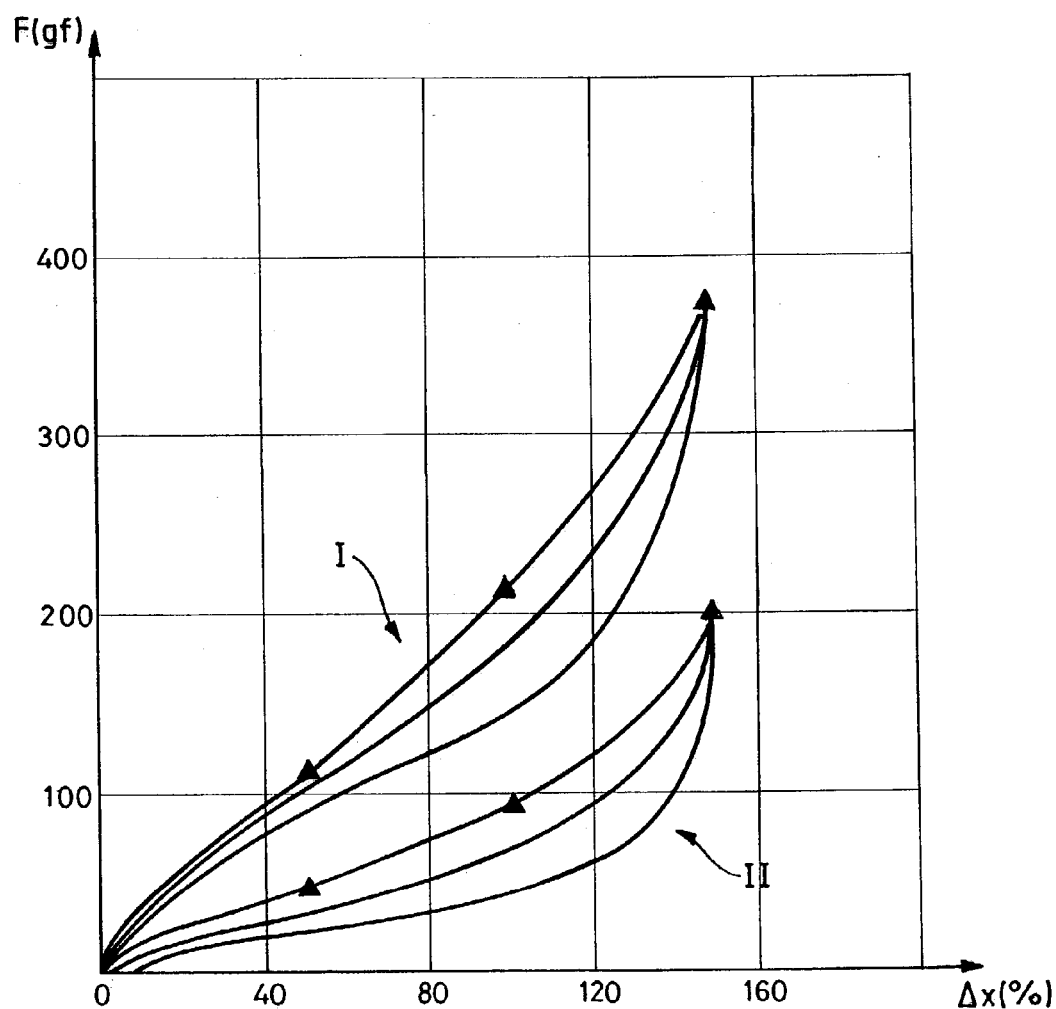
FIG_2

PLACEBO-TYPE COMPRESSION ORTHOSIS

This is a nationalization of PCT/FR01/00567, filed Feb. 27, 2001 and published in French.

The invention relates to the field of compressive ortheses for one or both lower limbs, generally known as "elastic stockings" or as "elastic tights".

Although the term "stockings" is used below, the invention is not limited to a particular article, but applies equally well to all compressive ortheses, whether in the form of tights, one-legged tights, stockings, or socks.

"Elastic stockings" are surgical stockings producing a therapeutic effect by compressing the lower limbs, and they are conventionally distinguished both from "fashion stockings" and from "support stockings" (also known as "anti-fatigue stockings"). Surgical elastic stockings are stockings that exert pressure of more than 10 millimeters of mercury (mmHg) to 36 mmHg as measured at the ankle (equivalent to 13 hectopascals (hPa) to 48 hPa; the present description nevertheless uses mmHg as the unit for measuring pressure, given that this usage is universal in the field of phlebology and medical compression). In addition, elastic stockings exert pressure that decreases going from the ankle towards the thigh.

At the ankle, support stockings exert a pressure of only 6 mmHg to 14 mmHg, while fashion stockings exert a pressure of 1 mmHg to 4 mmHg.

In order to apply a high level of compression on the lower limbs, elastic stockings are made of an elastic material, typically a knit of very tight texture associated with an incorporated elastic weft yarn (generally covered elastane) of large weight per unit length.

That particular structure gives an elastic stocking a visual appearance and feel that are particular and recognizable, and that are very different from those of a support stocking, and a fortiori of a fashion stocking.

One of the objects of the invention is to propose a structure for a knitted product that presents substantially the same shape, the same appearance, and the same feel as a surgical elastic stocking but which, unlike such a stocking, exerts insufficient pressure on the lower limbs to give rise to any significant therapeutic effect.

The purpose of such a product is to constitute a "textile placebo" for clinical tests designed to show the therapeutic effects of surgical elastic stockings, in application of methodology of the "double blind test versus placebo" type, of the kind commonly used for measuring the effect of the active principles used in medication.

One such placebo study is described for example by M. Chauveau and F. Agbomsom in "Force de compression et symptomatologie de l'insuffisance veineuse fonctionnelle des membres inférieurs: efficacitécomparée de six degrés de contention" [Compression force and functional venous insufficiency symptomatology of the lower limbs: a comparison of the effectiveness of six degrees of compression], published in *Phlébologie*, 1997; 50: 731–736.

Nevertheless, that study was carried out to show the effectiveness of support stockings which can easily be substituted by placebo stockings in the form of a fashion stocking having the same color and the same texture. Support stockings and fashion stockings are very similar in terms of appearance and feel and are easily substituted for each other while complying with the requirements of a double blind test with crossover.

That is not true of genuine elastic stockings which are very different from support stockings both in appearance and in feel.

A double blind test versus placebo thus requires a product to be available that has the same visual appearance and the same feel as an active stocking but which provides negligible compression, while nevertheless not being distinguishable a priori from an active stocking either by the patient or by the doctor prescribing the placebo compression, in order to comply with the procedures of a double blind test.

In order to present similar appearance and feel with an elastic stocking, a placebo stocking must be knitted using the same structure as an elastic stocking (plain stitch or micromesh combined with an elastic weft yarn). However unlike an elastic stocking, it must provide pressure at the ankle of less than about 5 mmHg (it has been shown that hemodynamic phenomena begin at about 7 mmHg).

In addition, and preferably, unlike an elastic stocking, a placebo stocking should not be degressive, i.e. pressure at the thigh should be of the same order as pressure at the ankle, typically with a thigh/ankle degressivity ratio lying in the range 0.8 to 1.1. Nevertheless, it should be observed that at low pressure values, differences between the ankle and the thigh are often smaller than the precision of test instruments, which makes it difficult in practice to verify accurately the results that are obtained concerning this parameter.

Furthermore, for obvious reasons of convenience and manufacturing costs, it is desirable for placebo stockings to be capable of being knitted on the same machines as elastic stockings, without major modification to the programming thereof.

According to the invention, these multiple and often contradictory requirements are solved by providing a stocking by knitting a knitting yarn combined with an extensible weft yarn, the stocking being of the placebo type and suitable for exerting compression pressure at the ankle of less than 8 mmHg, and preferably less than 5 mmHg.

According to various other characteristics of the invention:
- the ratio of compressive pressures between the thigh and the ankle is less than 125%, and preferably less than 110%;
- the ratio of compressive pressures between the thigh and the ankle is not less than 80%;
- the weft yarn presents a mass per unit length, measured under no tension, lying in the range 250 dtex to 600 dtex, and preferably lying in the range 350 dtex to 500 dtex;
- the weft yarn presents a proportion of elastic material below 25%, and preferably below 20% of the total weight of the yarn; and
- the weft yarn presents elongation capacity lying in the range 200% to 350%, an preferably lying in the range 200% to 300%.

There follows a description of various examples implementing the invention and given with reference to the accompanying drawing.

FIG. 1 shows the general stitch structure for an elastic stocking.

FIG. 2 is a graph plotting comparative elongation characteristics for a genuine elastic stocking and for a placebo stocking of the invention.

Figure 3:
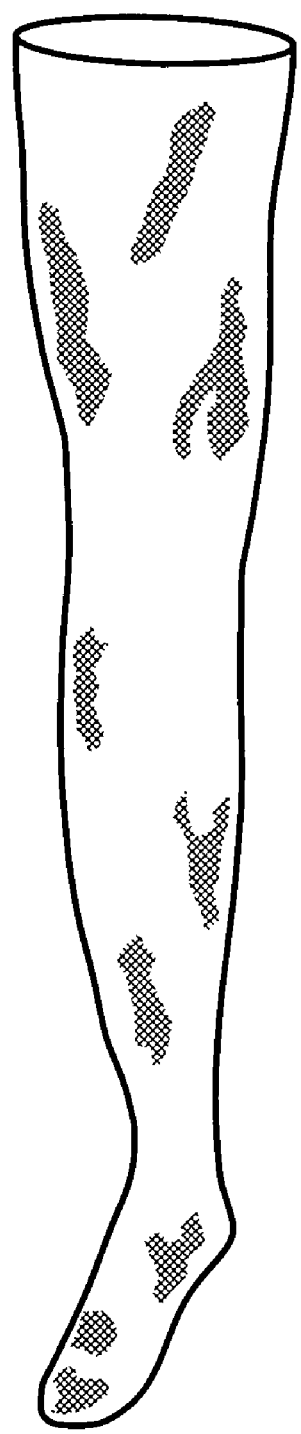
FIG. 3 shows a stocking of the invention.

The placebo stocking of the invention is made using a structure as shown in FIG. 1, similar to that of a conventional elastic stocking.

This is a structure knitted using a knitting yarn 10, e.g. in plain stitch, and in combination with a weft yarn 12 of covered elastane to produce the desired compression.

The invention relates to the particular weft yarn 12 that is selected, which yarn must ensure that the article is similar in appearance and feel to a conventional elastic stocking, while nevertheless presenting compression and degressivity properties that are quite different therefrom.

A series of examples are described below implementing various yarns selected to provide properties that are very different.

EXAMPLE 1

As a reference, a conventional class I (French classification) elastic stocking was made using the following yarns.

The knitting yarn (which is the same in all of the examples below) was a 17 dtex elastane yarn sold under the Lycra trademark (registered by Dupont de Nemours) with a 42/46 strand SFT PA 6.6 covering (i.e. covered in 42 dtex polyamide yarn with false twist in the S direction).

The weft yarn was an elastane yarn with two coverings having the following characteristics:
- a 310 dtex elastane core;
- 1/3.3 stretch;
- lower covering (LC) 1/22/7 ZFT PA 6.6 (1 yarn 22 dtex 7 strands Z direction false twist polyamide 6.6);
- upper covering (UC) 1/22/7 ZFT PA 6.6.

The weight of the resulting yarn was 400 dtex with 62% elastane and 38% polyamide. Its elongation capacity was about 250% to 300%.

The yarn obtained in that way presented an elongation characteristic as plotted at I in FIG. 2, where force is plotted as a function of deformation percentage (the characteristic presents a certain amount of natural hysteresis).

The characteristic was measured using a constant-elongation gradient dynamometer on a yarn spiral having a circumference of 2 meters (m) and doubled back eight times (the force exerted on a section of the yarn was thus 1/16th of the force exerted by the dynamometer), with the yarn being stretched to 150%.

The result obtained gives a visual indication of the "springiness" (stiffness) of the yarn, which increases with increasing elastane percentage in the weight of the yarn.

Using the two above-described yarns, a stocking was knitted presenting the following characteristics:
- width: 10.7/15/19.5 mm (width respectively at the ankle, at the calf, and at the thigh);
- length: 125/25/68 mm (ditto).

After being shaped and dyed in conventional manner, such a stocking provided pressure at the ankle greater than 10 mmHg, with ankle/thigh degressivity of 75%, and thus complied with the specifications for an elastic stocking of class I.

EXAMPLE 2

For reference purposes, a stocking was made having no weft yarn 12. Such a stocking does indeed deliver practically no compressive pressure (about 1 mmHg). However because of the absence of the elastic weft, that fabric is immediately recognizable because of its lack of firmness, being similar to that of a fashion stocking and thus unsuitable for the intended purpose.

EXAMPLE 3

In this example, attempts were made to reduce the weight of the elastane in proportion to the desired reduction in compressive pressure.

Thus, compared with the class I elastic stocking of Example 1 providing pressure at the ankle of 10 mmHg, the weight of the elastane yarn was divided by two with the difference being made up by increasing the proportion of polyamide.

An essential condition for obtaining a satisfactory placebo stocking is that is should be made from yarn presenting mass per unit length that is similar to that of a yarn used for making a conventional elastic stocking, so as to conserve the same visual appearance.

Another condition is that the yarn of the placebo stocking should have elongation capacity that is identical to that of yarn for an elastic stocking so that it can be knitted under the same conditions as said other yarn.

Other things remaining equal, the weft yarn of Example 1 (310 dtex elastane core having a weight at rest of 400 dtex) was replaced by yarn having the following composition:
- 156 dtex elastane core;
- 1/2.65 stretch;
- 1/33/20 FT PA 6.6 LC;
- 1/33/20 FT PA 6.6 HC.

The stocking was knitted in identical manner as before.

After shaping and dying, pressure measured at the ankle was 5.2 mmHg and pressure at the thigh was 3.72 mmHg, giving degressivity of 71%.

The stocking made in this way was satisfactory in terms of pressure at the ankle, but not satisfactory in terms of degressivity, being too far removed from the ideal value of 100% (in practice it is considered that the value should lie in the range 0.8 to 1.1 in order to be satisfactory).

Tests were performed by varying the stretch of the 150 dtex elastane yarn, but they did not enable a satisfactory result to be obtained. By reducing the value of the stretch to 1/2.5, the elongation capacity of the yarn is no longer satisfactory for it to be practical to make a pair of tights.

EXAMPLE 4

To mitigate the limitations mentioned above, the weight of the elastane yarn was reduced further.

In this example, the following composition was selected for the weft yarn:
- 78 dtex elastane core;
- 1/3.5 stretch;
- 2/33/20 FT PA 6.6 LC;
- 2/33/20 FT PA 6.6.HC.

Such a yarn presented mass per unit length at rest of 480 dtex, thus presenting an elastane content of 16%.

The elongation characteristic of that yarn is given at II in FIG. 2, which shows the large difference in springiness compared with a yarn for a class I elastic stocking (characteristic I in FIG. 2).

This yarn was used to knit a stocking having width of 9.4/13.2/16.3 mm.

After shaping and dying, that stocking provided pressure at the ankle of 4.9 mmHg an at the thigh of 2.7 mmHg, so its degressivity was 55%.

Since this degressivity value was still unsatisfactory, its width was modified to values of 10.5/14/17 mm. After shaping and dying the pressure measured at the ankle was 3.7 mmHg and at the thigh 2.4 mmHg, giving degressivity of 65%.

Another test was performed using the same yarn and the same width values as above, but with shaping and without dying: pressure at the ankle was then 2.8 mmHg and degressivity 118%.

Another test was performed by modifying the width at the calf and at the thigh giving width dimensions of 10.5/12.6/15.9 mm. After shaping and prior to dying pressure at the ankle was 3.9 mmHg and degressivity was 74%. After dying pressure at the ankle was 3.0 mmHg and degressivity 103%.

Finally adding a softening agent after dying changed the above parameters slightly: with 6% softening agent (as compared with 1.5% in a normal method) pressure at the ankle was reduced to 2.8 mmHg and degressivity to 87%.

Those various tests show that once the weft yarn has been selected on the basis of the criteria given above, it is possible to obtain fine adjustment for the values obtained for pressure at the ankle and for degressivity by acting on various parameters such as ankle/calf/thigh knitting widths, shaping temperature, dying parameters, adding a softening agent and concentration thereof, etc.

In any event, in order to retain a mass per unit length close to that of an elastic stocking yarn with comparable elongation capacity, it appears to be necessary to vary the springiness of the yarn, and in particular it should be reduced in order to ensure that the stocking is ineffective in providing hemodynamic therapy.

The weight of the elastane core could indeed be reduced further, e.g. by selecting a 44 dtex core with double covering, each covering yarn itself being made up of two 78 dtex polyamide yarn.

The invention claimed is:

1. A compressive orthosis stocking made by knitting a knitting yarn together with an extensible weft yarn, the extensible weft yarn comprising:
    a proportion of elastic material below 25% of the total weight of the yarn,
    a mass per unit length, measured under no tension, in the range 250 dtex to 600 dtex, and
    an elongation capacity in the range 200% to 350%;
    wherein the orthosis is suitable for exerting compressive pressure at the ankle of less than 8 mmHg, and
    wherein the orthosis is a placebo type stocking ineffective in providing hemodynamic therapy.

2. The orthosis of claim 1 suitable for exerting compressive pressure at the ankle of less than 5 mmHg.

3. The orthosis of claim 1 wherein the mass per unit length is in the range of 350 dtex to 500 dtx.

4. The orthosis of claim 1 wherein the proportion of elastic material is below 20% of the total weight of the yarn.

5. The orthosis of claim 1 wherein the elongation capacity is in the range 200% to 300%.

6. The orthosis of claim 1 wherein the ratio of compressive pressures between the thigh and the ankle is less than 110%.

7. The orthosis of claim 1 wherein the ratio of compressive pressures between the thigh and the ankle is not less than 80%.

8. A compressive orthosis stocking made by knitting a knitting yarn together with an extensible weft yarn, the extensible weft yarn comprising:
    a proportion of elastic material below 25% of the total weight of the yarn,
    a mass per unit length, measured under no tension, in the range 250 dtex to 600 dtex, and
    an elongation capacity in the range 200% to 350%;
    wherein the orthosis is suitable for exerting compressive pressure at the ankle of less than 8 mmHg, and
    wherein the orthosis is a placebo type stocking ineffective in providing hemodynamic therapy and wherein the ratio of compressive pressures between the thigh and the ankle is less than 125%.

* * * * *